United States Patent [19]
Patel et al.

[11] Patent Number: 5,726,137
[45] Date of Patent: Mar. 10, 1998

[54] LOW SILICONE HAIR CONDITIONING SHAMPOO AND NON-SILICONE HAIR CONDITIONING/STYLE CONTROL SHAMPOO

[75] Inventors: Amrit Patel, Dayton; Clarence R. Robbins, Martinsville, both of N.J.

[73] Assignee: Colgate-Palmolive Company, New York, N.Y.

[21] Appl. No.: 714,928

[22] Filed: Sep. 27, 1996

Related U.S. Application Data

[63] Continuation of Ser. No. 440,572, May 15, 1995, abandoned, which is a continuation-in-part of Ser. No. 155,251, Nov. 19, 1993, abandoned, which is a continuation-in-part of Ser. No. 984,786, Dec. 3, 1992, Pat. No. 5,346,642, which is a continuation-in-part of Ser. No. 507,335, Apr. 9, 1990, Pat. No. 5,213,716, which is a continuation-in-part of Ser. No. 369,361, Jun. 21, 1989, abandoned, Ser. No. 369,389, Jun. 21, 1989, abandoned, Ser. No. 432,644, Nov. 7, 1989, Pat. No. 5,051,250, and Ser. No. 432,952, Nov. 7, 1989, abandoned.

[51] Int. Cl.⁶ .................. C11D 1/94; C11D 3/37; C11D 1/40; C11D 3/43
[52] U.S. Cl. ............ 510/122; 510/124; 510/125; 510/127; 510/137; 510/158; 510/159; 424/70.11; 424/70.12; 424/70.21; 424/70.24; 424/70.27; 514/881
[58] Field of Search ................ 510/122, 124, 510/125, 127, 137, 158, 159; 424/70.11, 70.12, 70.21, 70.24, 70.27; 514/881

[56] References Cited

U.S. PATENT DOCUMENTS

| | | | |
|---|---|---|---|
| 4,554,098 | 11/1985 | Klisch et al. | 252/547 |
| 4,704,272 | 11/1987 | Oh et al. | 424/70 |
| 4,719,104 | 1/1988 | Patel | 424/70 |
| 4,728,457 | 3/1988 | Fieler et al. | 252/174.15 |
| 4,741,855 | 5/1988 | Grote et al. | 252/142 |
| 4,788,006 | 11/1988 | Bolich, Jr. et al. | 252/550 |
| 4,832,872 | 5/1989 | Scandel | 252/547 |
| 4,835,148 | 5/1989 | Barford et al. | 514/179 |
| 4,871,536 | 10/1989 | Arraudeau et al. | 424/59 |
| 4,915,854 | 4/1990 | Mao et al. | 252/8.8 |
| 4,997,641 | 3/1991 | Hartnett et al. | 424/70 |
| 5,034,218 | 7/1991 | Duvel | 424/70 |
| 5,037,632 | 8/1991 | Gross et al. | 424/47 |
| 5,051,250 | 9/1991 | Patel et al. | 424/70 |
| 5,073,274 | 12/1991 | Caswell | 252/8.6 |
| 5,078,990 | 1/1992 | Martin et al. | 424/70 |
| 5,104,642 | 4/1992 | Wells et al. | 424/47 |
| 5,106,613 | 4/1992 | Hartnett et al. | 424/71 |
| 5,114,706 | 5/1992 | Duvel et al. | 424/70 |
| 5,139,037 | 8/1992 | Grollier et al. | 132/203 |
| 5,213,716 | 5/1993 | Patel et al. | 252/547 |
| 5,221,530 | 6/1993 | Janchitraponvej | 424/70 |
| 5,275,761 | 1/1994 | Bergmann | 252/551 |
| 5,346,642 | 9/1994 | Patel et al. | 252/174.21 |
| 5,393,519 | 2/1995 | Dowell et al. | 424/70.11 |
| 5,587,154 | 12/1996 | Dowell et al. | 424/70.11 |
| 5,665,267 | 9/1997 | Dowell et al. | 510/123 |

FOREIGN PATENT DOCUMENTS

| | | |
|---|---|---|
| 0437114 | 7/1991 | European Pat. Off. . |
| 511652 | 11/1992 | European Pat. Off. . |
| 9210162 | 6/1992 | WIPO . |
| 9308787 | 5/1993 | WIPO . |
| 9401077 | 1/1994 | WIPO . |

OTHER PUBLICATIONS

Kosemtika Aerosole Riechstuffe; Journal: Seifen, Oele, Fette, Wache Oct., 1984, vol. 110, No. 17 "Liquivat Brands"; Seib Vogel.

LesLuviquat; Cationigues Pour Soins Capillaries; Journal: Parfums, Cosmet Aromes; Nov.; 1988, vol. 83, pp. 99–100, 102 "Cationic Luviquats for Hair Care" Frosch.

Primary Examiner—Paul Lieberman
Assistant Examiner—Gregory R. Delcotto
Attorney, Agent, or Firm—Richard Ancel

[57] ABSTRACT

A mild, non-irriatating hair conditioning shampoo is disclosed comprising an aqueous dispersion of a water-insoluble lipid phase, an anionic hair cleansing surfactant, an amphoteric surfactant present at a level of at least about 0.75 parts by weight per part by weight of said anionic surfactant, at least one hair conditioning, film forming, polycationic polymer soluble in the aqueous dispersion and 0–6% by weight, based on the weight of the shampoo, of a water-insoluble, non-volatile hair conditioning silicone, the water-insoluble lipid phase comprising at least one lipid soluble, emulsifiable, monocationic, quaternary ammonium compound or amine solubilized in a water-insoluble long chain lipid compound, the weight ratio of monocationic compound to the lipid compound in the lipid phase being in the range of from about 5:1 to about 1:10 and the molar ratio of anionic surfactant to water-insoluble cationic compound is greater than 2:1. The shampoo having no silicone possesses a high degree of style control properties. The shampoo containing silicone has a high degree of hair conditioning properties.

18 Claims, No Drawings

LOW SILICONE HAIR CONDITIONING SHAMPOO AND NON-SILICONE HAIR CONDITIONING/STYLE CONTROL SHAMPOO

RELATED APPLICATIONS

This is a continuation of application Ser. No. 08/440,572 filed May 15, 1995 abandoned which is a CIP of copending U.S. Ser. No. 08/155,251, filed Nov. 19, 1993, which is a CIP of copending U.S. Ser. No. 07/984,786 filed Dec. 3, 1992, now U.S. Pat. No. 5,346,642 which is a CIP of U.S. Ser. No. 07/507,335 filed Apr. 9, 1990, now U.S. Pat. No. 5,213,716 which is a CIP of U.S. Ser. No. 07/369,361 filed Jun. 21, 1989 (Abandoned), U.S. Ser. No. 07/369,389 filed Jun. 21, 1989 (abandoned), U.S. Ser. No. 07/432,644 filed Nov. 7, 1989, now U.S. Pat. No. 5,051,250, and U.S. Ser. No. 07/432,952 filed Nov. 7, 1989 (abandoned).

BACKGROUND OF THE INVENTION

FIELD OF THE INVENTION

The present invention relates to hair conditioning shampoos containing little-or no water-insoluble silicone hair conditioning agents.

DISCUSSION OF THE PRIOR ART

So-called two-in-one hair conditioning shampoos which achieve hair conditioning as well as hair cleansing with one product have been formulated to overcome the disadvantages associated with the necessity for sequentially applying separate compositions to the hair to achieve these purposes; one is a shampoo to cleanse the hair and the other is a separate hair conditioner to condition the hair.

Certain cationic compounds and polymers have been found to be excellent hair conditioning agents. However, combining these agents in a shampoo formulation with anionic surfactants which have been found to be the most effective for removing sebum, soil and other atmospheric contaminants gives rise to inherent incompatibility problems between the two types of agents. Contact between a negatively charged anionic surfactant and a positively charged cationic surfactant or cationic polymer produces a precipitate that forms immediately or causes an interaction between the anionic and cationic compounds that significantly reduces their respective cleaning and conditioning properties. The reduction in cleansing and conditioning effectiveness is observed even in compositions wherein the anionic and cationic compounds do not precipitate from the composition, but remain in solution or suspension. This incompatibility between an anionic surfactant and a cationic conditioning compound is well recognized by those skilled in the art. For example, in *Cosmetics*, Interscience Publishers, Inc., New York, p. 538 (1957), author Sagarin states that anionic and cationic compounds cannot be used in combination because they react to form insoluble salts.

A partial solution to this incompatibility problem in the formulation of conditioning shampoos lies in substituting nonionic, amphoteric or zwitterionic surfactants for the conventionally employed anionic surfactants in shampoos containing cationic conditioning agents. See, e.g., U.S. Pat. Nos. 3,849,348 (Hewitt); 3,990,991 (Gerstein); and 3,822,312 (Sato).

Another difficulty inherent in formulating a conditioning shampoo is an instability problem that results when water-insoluble conditioning agents are also included in the conditioning shampoo composition, such as the non-volatile silicones that are well recognized in the art as providing a degree of softness to the hair.

Silicones in shampoo compositions have been disclosed in a number of prior patents, i.e., U.S. Pat. Nos. 2,826,551 (Green); 3,964,500 (Drakoff); 4,364,837 (Pader); 4,741,855 (Grote et al); 4,788,006 (Bolich, Jr. et al); 4,902,499 (Bolich, Jr. et al); 4,704,272 (Oh et al); and British Patent No. 849,433 (Woolston).

A particularly difficult obstacle to overcome in silicone-containing conditioning shampoos is that of maintaining a dispersed, insoluble, non-volatile silicone material suspended in stable form while retaining the cleansing and conditioning performance of the conditioning shampoo. The stability barrier is particularly prevalent in conditioning shampoos containing an anionic surfactant and a cationic conditioning material which, as outlined above, by themselves tend to interact and present stability dilemmas. A variety of materials have been proposed for inclusion in silicone containing conditioning shampoos for purposes of thickening and stabilization such as xanthan gum, long chain acyl derivatives, long chain amide oxides, and long chain alkanolamides such as those disclosed in, e.g., U.S. Pat. Nos. 4,788,006, 4,704,272 and 4,741,855 mentioned hereinabove.

There are also environmental concerns associated with the use of silicones inasmuch as they are not easily biodegraded. Furthermore, processing problems arise when using silicones, particularly high viscosity silicones. Finally, it is difficult to remove silicones from the hair, thereby reducing the effectiveness of perming and coloring processes.

Numerous attempts have been made to provide so-called three-in-one shampoo compositions, i.e., shampoo formulations which will provide not only hair cleansing action, but also hair conditioning effects and style control or set and curl retention of the hair following completion of the shampooing and rinsing operations.

Hair conditioning effects are usually described as softness and smoothness of the hair after washing, a less sticky feeling, easy passage of the comb through the hair, a less hard or rough feeling after shampooing, relief from static electricity or "fly-away" and manageability.

Hair styling, i.e., hair style retention or hold or set and curl retention can be accomplished in two ways. First, the hair can be subjected to a permanent chemical alteration to achieve a certain desired shape. Secondly, a temporary alteration of the shape of the hair can be achieved, generally by applying to the hair a third composition following shampooing and/or the application of a hair conditioning agent. The materials comprising these temporary style control compositions have traditionally been resins, gums, etc., and are usually applied to the previously shampooed and/or conditioned hair in the form of mousses, gels, lotions or sprays. Drying the thus-treated hair results in a "set" of the resinous or gum material to a stiff condition which temporarily holds the hair in the desired shape.

The temporary style control agents differ from the permanent style control treatments in that the latter are marginally affected by subsequent shampooing operations, whereas the temporary agents are completely removed upon shampooing thereby requiring their re-application after every shampoo operation in order to maintain the desired style control.

One type of temporary style control agent are the adhesive polymers which generally comprise a non-water solvent, and a soluble rigid polymer having a glass transition temperature above the temperature normally reached in styling operations, i.e., blow drying, etc. Examples of such polymers are those described in U.S. Pat. Nos. 3,743,715, 4,165,367 and 4,223,039.

Other polymers heretofore suggested for temporary style control are multi-component polymers which combine up to four or more monomers. Exemplary of these types of style control polymer systems are those disclosed in U.S. Pat. Nos. 3,222,329, 3,577,517, 4,012,501 and 4,272,511.

Block copolymers having multiple glass transition temperatures have also been employed as style control agents, such as those described in U.S. Pat. Nos. 3,907,984, 4,030,512 and 4,283,384.

U.S. Pat. No. 5,104,642 describes the use in a hair styling composition of a polymer comprising up to 50% of a first polymerizable hydrophilic monomer and the remainder a second polymerizable hydrophilic monomer, the resulting polymer having a molecular weight of 5,000 to 1,000,000, a glass transition temperature, Tg, of greater than −20° C. and a solubility parameter of 8.5 to 12.0. International Application No. PCT/US91/02170, published Oct. 17, 1991, discloses the incorporation of these types of polymers in a hair shampoo formulation.

Canadian Patent No. 2,033,626 describes a shampoo composition which provides set and curl retention comprising at least one anionic surfactant, a film-forming polymer (e. g. Polymer JR, GAFQUAT 755, MERQUAT 550, chitosan or its derivatives, CROQUAT S, LAMEQUAT L or methylvinyl imidazolium chloride/vinyl pyrrolidone copolymer) and large amounts of citric acid to enhance the effect of the film-forming polymer. There is no disclosure in the patent that hair conditioning properties are possessed by the shampoo formulation.

It is an object of the present invention to provide a hair conditioning shampoo which solves the above-noted prior art problems.

It is another object of the invention to provide a hair conditioning shampoo having a high degree of hair conditioning activity and a hair conditioning shampoo which provides style control.

A third object of the invention is to provide a hair conditioning shampoo which is less irritating to the scalp than conventional shampoos of this type.

SUMMARY OF THE INVENTION

These and other objects are realized by the present invention which relates to an aqueous dispersion of a water insoluble lipid phase, about 3 to 25% by weight an anionic hair cleansing surfactant, an amphoteric surfactant present in said dispersion at a level of at least about 0.75 parts by weight per part by weight of said anionic surfactant, at least one hair conditioning, film-forming, polycationic polymer and 0–6% by weight, based on the weight of the shampoo, of a water-insoluble, non-volatile silicone hair conditioning agent; said polycationic polymer being soluble in said aqueous detergents; said water-insoluble lipid phase comprising at least one lipid-soluble, emulsifiable, monocationic quaternary ammonium compound or amine solubilized in a water-insoluble, long chain lipid compound, the weight ratio of monocationic compound to said lipid compound in said lipid phase being in the range of from about 5:1 to about 1:10 and the molar ratio of anionic surfactant to water-insoluble cationic compound is greater than 2:1, preferably from about 2:1 to about 50:1 and most preferably from about 5:1 to about 30:1.

DETAILED DESCRIPTION OF THE INVENTION

The invention is predicated on the discovery that in an aqueous hair conditioning shampoo containing anionic surfactants and detergent-soluble polycationic conditioning agents and relatively low amounts of a water-insoluble, nonvolatile silicone hair conditioning agents, the presence in the shampoo of a water-insoluble lipid phase having dissolved therein a monocationic, lipid soluble hair conditioning agent results in a hair conditioning shampoo with enhanced hair conditioning and hair cleansing properties, while avoiding many of the instability and reduced effectiveness drawbacks associated with conventional two-in-one shampoo formulations.

It has unexpectedly been found that in the hair conditioning shampoo of the invention, the lipid solubilized monocationic compound acts synergistically rather than competitively with the water-soluble polycationic polymeric agents to provide an enhanced hair conditioning effect over that provided by conventional hair conditioning shampoos, while employing very little silicone co-conditioners.

Moreover, it is believed that the presence of the lipid phase acts to greatly reduce the inherent instability of anionic surfactant/cationic conditioner combinations by limiting contact between the respective oppositely charged species in the formulation. The lipid phase containing the monocationic agent appears to function in the formulation as a water-insoluble conditioner, much like a silicone for example, but without the disadvantages associated with typical water-insoluble conditioning agents, such as instability, the tendency to leave an uneven coating on the hair, etc.

Most unexpectedly, it has been found that the absence of a water-insoluble, non-volatile silicone hair conditioning agent from the above-described formulation imparts style control properties to the shampoo. It was also unexpectedly found that the absence of silicone from the shampoo formulation of the invention results in a high degree of hair damage repair, including split end repair, as well as higher style retention.

A critical feature of the present invention resides in the lipid/lipid-soluble monocationic conditioning agent phase of the hair conditioning shampoo.

Suitable lipid-soluble monocationic compounds for inclusion in the lipid phase of the shampoo include any of the aliphatic long chain, monocationic, quaternary ammonium compounds or amines having at least one long chain aliphatic group, preferably alkyl, having an average of from about 16 to about 40 carbon atoms. Amines having appropriate pKa values, i.e., at least about 7.5, would where the pH of the shampoo formulation is 6 or less, be partially protonated, thereby providing the necessary cationic charge to function as a hair conditioning agent.

The hair conditioning shampoo of the present invention may include any of the conventional adjuvants normally employed in such shampoos such as those disclosed in U.S. Pat. No. 5,078,990.

For example, an amphoteric surfactant is included in the formulation as a co-surfactant. In certain preferred shampoo formulations (see Examples 1, 5 and 7 hereinbelow), the amphoteric surfactant is the principal detergent.

Suitable such amphoteric surfactants include those corresponding to the formula:

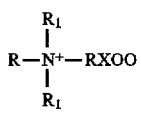

wherein R is a $C_8-C_{18}$ alkyl or $C_8-C_{18}$ alkanolamido $C_2-C_3$ alkyl, $R_1$ is $C_1-C_3$ alkyl, $R_2$ is a $C_1-C_4$ alkylene or $C_1-C_4$ hydroxy alkylene and X is C or S. When X is C, the detergent is called a betaine and when X is S, the detergent is called a sultaine or sulfobetaine. These detergents can be described broadly as derivatives of aliphatic quaternary ammonium or tertiary sulfonium compounds containing a $C_8-C_{18}$ aliphatic radical which may be straight chained or branch chained and containing an anionic group. Preferred betaine and sultaine detergents are cocoamidopropylbetaine, lauryldimethylammonioacetate, myristyldimethylammonioacetate, $C_8-C_{18}$ alkanamidopropyldimethylammonioacetate, 1-(myristyldimethylammonio) -propane-3-sulfonate and 1-(myristyldimethylammonio) -2-hydroxypropane-3-sulfonate.

U.S. Pat. No. 5,078,990 (Martin et al), the disclosure of which is incorporated herein by reference, discloses that an aqueous shampoo containing a long chain alkyl sulfate and/or long chain alkyl ether sulfate anionic surfactant and a cationic di-long chain alkyl quaternary ammonium nitrogen-containing compound, unexpectedly increases the ability of the aqueous shampoo to (1) incorporate water insoluble conditioning agents, particularly non-volatile silicone materials, and (2) remove previously applied conditioning agents and other soiled conditioning agents and contaminants from the hair. The patent, however, requires the presence of a water-insoluble conditioning agent and specifies that the molar ratio of anionic surfactant to long chain quaternary ammonium compound is at least about 85:1, and preferably higher. Any of the long chain quaternary ammonium monocationic compounds disclosed in U.S. Pat. No. 5,078,990 may be utilized in the practice of the present invention.

Preferred among the monocationic compounds are distearyldimethylammonium, dicetyldimethylammonium, tricetylmethylammonium, behenyltrimethylammonium, cetyltrimethylammonium, hexadecyl trimethylammonium, stearyl benzyl dimethylammonium, cetyl pyridinium salts, e.g., chlorides, bromides, etc. Suitable amines include distearylamine, distearylmethylamine, behenylamine, behenylmethylamine, behenyldimethylamine, dicetylamine, dicetylmethylamine, tricetylamine, etc.

Suitable lipids include long chain aliphatic $C_{24}-C_{50}$ alcohols, long chain aliphatic acylated ingredients, e.g., esters and amides with at least one long chain greater than about 24 carbon atoms, i.e., ethylene glycol distearate, glyceryl tristearate, beeswax, isosteareth-2, isosteareth-10, petrolatum, isostearyl lactate, isopropyl isostearate, isocetyl stearate, ethoxylated alcohols, e.g., alcohols having a chain length equal to or greater than 16 carbon atoms wherein the number of ethoxy groups may vary up to a maximum of about 40, and long chain aliphatic acids, e.g., carboxylic acids having chain lengths of from about 16 to about 40 carbon atoms.

The shampoo is formulated such that the weight ratio of monocationic compound to lipid compound is in the range of from about 5:1 to about 1:10. The shampoo should, however, contain at least about 0.7% by weight of the monocationic compound to ensure a sufficiently high degree of hair conditioning effect. It has been found that employing less than about 0.7% by weight of monocationic compound results in a shampoo which does not sufficiently condition hair to avoid problems of, e.g., "fly-away."

Generally, the lipid phase comprises from about 1% to about 16% by weight, and preferably from about 4% to about 10% by weight of the shampoo formulation.

Any of the conventionally employed anionic surfactants may be utilized in the shampoo of the present invention. Typical of these surfactants are those set forth in U.S. Pat. No. 4,554,098, the entire disclosure of which is incorporated herein by reference. Suitable such anionic surfactants include the water-soluble salt of a sulfuric acid ester of the reaction product of one mole of a $C_{10}-C_{16}$ alkanol with 5 to 12 moles of ethylene oxide. These detergents are described in the prior art as alkyl ether sulfates of the following structural formula: $R(OC_2H_4)_nOSO_3M$, wherein R is an alkyl containing about 10 to about 16 carbon atoms, n has an average value of 5 to 12 and M is a cation. Usually, the cation will be selected from the group consisting of sodium, potassium, ammonium and mono-, di- and triethanolammonium.

Preferably, the alkyl ether sulfates will contain 12 to 14 carbon atoms in the alkyl group and will be employed in the form of the sodium or ammonium salt. Examples of suitable alkyl ether sulfates are sodium $C_{12}-C_{14}$ alkyl ethylenoxy (6.5) sulfate, ammonium $C_{12}-C_{14}$ alkyl ether ethylenoxy (6.5) sulfate, sodium $C_{12}-C_{14}$ alkyl ether ethylenoxy (9.5) sulfate, sodium $C_{12}-C_{14}$ alkyl ether ethylenoxy (11.4) sulfate, potassium $C_{12}-C_{16}$ alkyl ether ethylenoxy (6.5) sulfate, ammonium $C_{12}-C_{13}$ alkyl ether ethylenoxy (6.5) sulfate and ammonium $C_{12}-C_{16}$ alkyl ether ethylenoxy (7) sulfate. Preferred alkyl ether sulfates are the sodium and ammonium $C_{12}-C_{13}$ or $C_{12}-C_{14}$ alkyl ether ethylenoxy (6.5–9) sulfates.

Additional anionic detergents are water-soluble, non-soap, anionic detergents having in their molecular structure a $C_7-C_{22}$ alkyl, alkenyl or acyl group and a sulfonate, sulfate or carboxylate group. Such detergents are employed in the form of water-soluble salts and the salt-forming cation is usually selected from the group consisting of sodium, potassium, ammonium, and mono-, di- or tri-$C_2-C_3$ alkanolammonium, with the sodium and ammonium cations again being preferred.

Suitable such anionic detergents include the following:

1. The $C_8-C_{18}$ alkyl sulfates which are usually obtained by sulfating $C_8-C_{18}$, alkanols obtained by reducing the glycerides of tallow or coconut oil. Preferred alkyl sulfates contain 10 to 16 carbons in the alkyl group.

2. The $C_9-C_{15}$ alkylbenzene sulfonates wherein the alkyl group is either a straight chain or a branched chain, with the straight chain being preferred for its improved biodegradability.

3. The $C_8-C_{22}$ olefin sulfonates which may be obtained by sulfating the appropriate olefin. Preferred olefin sulfonates contain from 14 to 16 carbon atoms in the alkyl group and are obtained by sulfonating an alpha-olefin.

4. The $C_8-C_{18}$, alkyl ether ethylenoxy sulfates of the formula:

$$R(OC_2H_4)_nOSO_3M$$

wherein n is 1 to 4. These sulfates differ from the primary alkyl ether sulfate detergent in the number of moles of ethylene oxide (1–4) reacted with one mole of alkanol in forming the ethoxylated alkanol which is sulfated and neutralized to form this anionic detergent. Preferred alkyl ether ethylenoxy sulfates contain 10 to 16 carbon atoms in the alkyl group and contain 2 to 3 ethylene oxide groups per mole of alkanol.

5. The $C_{10}$–$C_{20}$ paraffin sulfonates obtained, for example, by reacting an alpha-olefin with bisulfite. Preferred alkane sulfonates contain 13 to 17 carbon atoms in the alkyl group.

6. The $C_6$–$C_{12}$ phenyl ether polyethylenoxy sulfates containing from 2 to 6 moles of ethylene oxide in the molecule may also be used. These detergents can be prepared by reacting an alkyl phenol with 2 to 6 moles of ethylene oxide and sulfating and neutralizing the resultant ethoxylated alkylphenol. Preferred detergents in this group have 8 to 12 carbon atoms in the alkyl group and contain about 4 ethylene oxide groups in the molecule.

7. The $C_8$–$C_{18}$ alkyl sulfoacetates corresponding to the formula:

$$ROOCCH_2SO_3M$$

wherein R is a $C_8$–$C_{18}$, alkyl which may be prepared by esterifying an alkanol with chloroacetic acid or chloroacetyl chloride and then reacting the chloroester with a sodium or potassium bisulfite. Preferred sulfoacetates contain 12 to 16 carbon atoms in the alkyl group.

8. The N-mono-$C_8$–$C_{22}$ alkyl (includes alkyl groups interrupted by an ether or amido group) sulfosuccinates prepared by reacting, for example, either one mole of $C_8$–$C_{18}$ alkanol or a $C_8$–$C_{18}$ alkoxy $C_2$–$C_3$ alkanol or a $C_8$–$C_{18}$ alkanamido $C_2$–$C_3$ alkanol with maleic acid and reacting the resultant product with an alkali metal bisulfite to form an N-mono-$C_8$–$C_{22}$ alkyl sulfosuccinate. It should be recognized that the alkyl group of product made from the N-acyl alkanolamine will contain an amido intermediate linkage. Similarly, the alkyl group may be interrupted by an ether linkage or ester linkage if an alkyl ether ethanol or an alkyl ester of ethylene glycol is reacted with maleic acid. Preferred sulfosuccinates are disodium N-mono-$C_8$–$C_{18}$ acylisopropanolaminosulfosuccinate, disodium lauryl sulfosuccinate and N-monooleylisopropanolaminosulfosuccinate.

9. The N-$C_8$–$C_{18}$, acyl sarcosines may be produced by neutralizing the reaction product of a $C_8$–$C_{18}$, alkanoic acid with N-methyl glycine. Preferred sarcosinates contain 12 to 14 carbon atoms in an acyl group obtained by reduction of coconut oil.

10. The N-$C_8$–$C_{18}$ acyl taurines may be produced by neutralizing the reaction product of a $C_8$–$C_{18}$, alkanoic acid with aminoethylsulfonic acid. Again, preferred taurates contain 12 to 14 carbon atoms in an acyl group obtained by reduction of coconut oil.

11. The O-$C_8$–$C_{18}$, acyl isethionates may be produced by neutralizing the reaction product of a $C_8$–$C_{18}$, alkanoic acid with 2-hydroxyethanesulfonic acid. Similar to the sarcosines and taurines, the preferred isethionates contain 12 to 14 carbon atoms in an acyl group obtained by reduction of coconut oil.

The anionic surfactant is generally present in an amount of from about 3% to about 25%, and preferably from about 7% to about 14% by weight of the shampoo formulation.

The combination of amphoteric and anionic surfactants provide a hair conditioning/style control shampoo which is milder and less irritating to the scalp than conventional such shampoos which contain an anionic surfactant as the major surfactant component. The amphoteric surfactant is present in the shampoo at a level of at least about 0.75 parts by weight per 1 part by weight of the content of anionic surfactant present in the composition. The preferred level of amphoteric surfactant is in the range of from about 0.75 to 1.25 parts by weight, more preferably from about 0.9 to 1.1 parts by weight per 1 part by weight of anionic surfactant. It has been found that the presence of one or more amphoteric surfactants at these levels tends to cancel out the tendency of most anionic surfactants to cause irritation when contacted with the skin or scalp.

Any of the conventional hair conditioning, film forming polycationic hair conditioning agents used in typical prior art hair conditioning shampoo formulations which are soluble in the aqueous surfactant phase of the composition may be employed in the practice of the present invention. Exemplary of these agents are Polyquaternium-10, Polyquaternium-7, (e.g., Merquat-550) and mixtures thereof. Polyquaternium-10 is a salt of hydroxyethyl cellulose reacted with trimethylammonium substituted epoxide.

Polyquaternium-7 is a copolymer of acrylamide and dimethyldiammonium chloride.

Generally, the polycationic quaternary ammonium polymers comprise from about 0.2 to about 3% by weight of the shampoo formulation.

Any suitable water-insoluble, non-volatile, conventional silicone hair conditioning agent may be employed in the shampoo of the invention and includes, e.g., either a polyalkyl siloxane, a polyalkylaryl siloxane or a polyether siloxane copolymer. Mixtures of these fluids may also be used. The silicones should also be insoluble in the shampoo matrix. This is the meaning of "insoluble" as used herein.

The essentially non-volatile polyalkyl siloxanes that may be used include, for example, polydimethyl siloxanes with viscosities ranging from about 5 to about 100,000 centistokes at 25° C. These siloxanes are available, for example, from the General Electric Company as the Vicasil series and from Dow Corning as the Dow Corning 200 series. The viscosity can be measured by means of a glass capillary viscometer as set forth in Dow Corning Corporate Test Method CTM0004 (Jul. 20, 1970).

The essentially non-volatile polyalkylaryl siloxanes that may be used include, for example, polymethylphenylsiloxanes having Niscosities of about 15 to about 85 centistokes at 25° C. These siloxanes are available, for example, from the General Electric Company as SF-1075 methyl phenyl fluid or from Dow Corning as 558 Cosmetic Grade Fluid.

The essentially non-volatile polyether siloxane copolymer that may be used is, for example, a dimethyl polyoxyalkylene ether copolymer fluid having a nominal viscosity of about 1,200 to about 1,500 centistokes at 25° C. This copolymer is available, for example, from the General Electric Company as SF-1066 organosilicone surfactant. Preferred compounds of this type are polypropylene oxide modified dimethylpolysiloxanes (e.g., Dow Corning DC-1248), although ethylene oxide or mixtures of ethylene oxide and propylene oxide may also be used.

It is also possible to use silicones in the present compositions which have amino-functional groups such as Dow Corning's X2-8107 material.

References disclosing suitable silicones include U.S. Pat. Nos. 2,828,551, 3,964,500 and 4,364,837, all of which are incorporated herein by reference.

Preferred silicones are dimethicone and dimethicone/polydimethyl siloxane.

The polycationic polymers disclosed in the aqueous surfactant phase of the shampoo and the lipid phase of the composition function as the primary stabilizers of the shampoo dispersion. A neutral polymer such as hydroxyethylcellulose may be combined with the polycationic polymer to enhance its stabilizing effect on the dispersion. It is a unique advantage of the present invention that the polycationic polymer, in addition to stabilizing the dispersion, also enhances the hair conditioning properties of the shampoo.

Additional amphoteric surfactants which may be employed in the shampoo of the invention include amine oxides such as the $C_8$-$C_{18}$ alkyl dimethylamine oxides.

Exemplary of other adjuvants are hydrotropes such as sodium cumene sulfonate, sodium xylene sulfonate, sodium benzene sulfonate and sodium hexyl sulfonate.

The invention is illustrated by the following nonlimiting examples.

EXAMPLE I

A hair conditioning shampoo having the following formulation was prepared:

| Part | Ingredient | Supplier, Tradename | Wt. % |
|---|---|---|---|
| 1 | Deionized Water | | 13.750 |
| | Ammonium Lauryl Sulfate | Henkel's Standepol A, 28% | 16.000 |
| | Sodium Deceth-3 Sulfate | Vista's Novel 10-44 E.S. Na, 30% | 15.000 |
| | Sodium Cumene Sulfonate | Stepan's Stepanate SCS, 43% | 7.000 |
| | $Na_4$ EDTA | Rhone-Poulenc's Cheelox SF-78 | ±0.100 |
| | $Na_2HPO_4$ | Sodium Phosphate Dibesic | 0.200 |
| | Cocamidopropyl Betaine #3 | Goldschmidt's Tego Betaine L-7, 30% | 30.000 |
| 2 | Deionized water | | 5.000 |
| | Polyquaternium-10 | Amerchol's Polymer JR-30M | 0.500 |
| 3 | Polyquaternium-7 | Calgon's Merquat-550, 8% | 2.500 |
| 4 | Isosteareth-2+ | Sherex's Varonic 66-E2 (1.5 EO) | 2.000 |
| | Compound 909* | Petrolite's C-7138 Polymer | 4.000 |
| | Distearyl Dimonium Chloride | Sherex's Arosurf TA-100 | 1.000 |
| 5 | Yellow Color (1% solution) | | 0.250 |
| | Perfume | | 1.200 |
| | Preservative, 50% aqueous solution | | 1.000 |
| | Sodium Cumene Sulfonate | Stepan's Stepante SCS, 43% | ±0.500 |
| TOTAL | | | 100.000 |

+Isosteareth-2 is ethoxylated isostearyl alcohol (1.5 EO units).
*Compound 909 is a $C_{20}$-$C_{40}$ aliphatic alcohol.

The main mixing vessel is stainless steel equipped with a variable speed Lightnin' Mixer and heating and cooling facilities. A separate stainless steel or plastic vessel was used for the Part 2 premix. A separate stainless steel vessel equipped with heating facilities and minimal mixing is employed for the Part 4 oil phase.

To the main mixing vessel was charged Part 1 formula amount of deionized water and mixing begun. In order, Part 1 formula amounts of ammonium lauryl sulfate, sodium deceth sulfate, sodium cumene sulfonate, $Na_4$, sodium phosphate dibasic and cocoamidopropyl betaine were added to the main mixing vessel, allowing sufficient time for each ingredient to completely dissolve before adding the next and taking care not to promote foam formation. The batch was mixed for at least 15 minutes before continuing. The batch was heated with mixing to 85°-87° C.

To a separate, dry, clean container, Part 2 formula amount of deionized water was charged. With mixing, Part 2 formula amount of Polyquaternium-10 was dispersed in the deionized water and mixed well until the premix was free of lumps, but not longer than 5 minutes just prior to addition, to avoid gelling. Part 2 premix was added to the main mixing vessel with mixing, taking care not to promote foam formation. The batch was mixed for at least 15 minutes before continuing. Mixing was continued with heating to 85°-87° C.

Part 3 formula amount of Polyquaternium-7 was added to the main mixer with mixing, taking care not to promote foam formation. The batch was mixed for at least 15 minutes before continuing. Mixing was continued with heating to 85°-87° C.

To a third, separate, heatable container, the formula amounts of all ingredients of the Part 4 oil phase were charged and heating begun. The ingredients were mixed well until all the material was melted and uniform at a temperature of 90°-92° C. When liquid and uniform, the mixture will not necessarily be clear; it may be translucent. When the batch was at 85°-87° C., Part 4 premix was added to the main mixing vessel with high-speed mixing, taking care not to promote foam formation. Heating was discontinued and the batch was mixed at temperature for at least 15 minutes. Then the batch was cooled with mixing.

Part 5 colors were added at any time during the cooling of the batch. When the batch was at 52° C., Part 5 formula amount of perfume was added to the batch and mixing and cooling were continued. When the batch was at or below 38° C. Part 5 formula amount of preservative was added to the batch with continued mixing and cooling.

Specifications were checked on a batch sample cooled to 25° C. and, if necessary, sodium cumene sulfonate was added to the main mixing vessel to reduce viscosity.

In the formulation of Example 1, two polycationic conditioners were employed at a total active concentration of 0.6% by weight [0.3% Polyquaternium-10 (Amercholls Polymer JR-30M) and 0. 3% Polyquaternium-7 (Calgon's Merquat-550, 8%)]

In the following tests, a variety of different polycationic conditioners were employed in the formulation of Example 1 at an active concentration of 0.6% by weight. The polycationics and the test results are set forth below:

| Polycationics | Relative Wet Combing Score |
|---|---|
| Polycationics of Example 1 | 4.5 |
| 0.6% Nerquat 550 | 6.0 |
| 0.6% Polymer JR-30M | 5.0 |
| 0.6% Polymer JR-400 | 3.5 |
| 0.6% Merquat-100 | 5.0 |

\* The higher wet combing scores indicate a higher level of conditioning. A score of 4.5 is approximately equivalent to commercial two-in-one conditioning shampoo containing silicone conditioners.

The formulation of Example 1 was varied to include identical levels of monofunctional cationic conditioners in place of the distearyldimethylammonium compound with the following results:

| Monocationies Score | Relative Wet Combing |
|---|---|
| Distearyldimethylammonium | 4.5 |
| Tricetyimethylammonium | 4.0 |
| Dicetyldimethylammonium | 3.5 |
| Behenyltrimethylammonium | 3.5 |
| Cetyltrimethylammonium | 3.0 |

The formulation of Example 1 was also varied to include other lipids in place of isosteareth-2 with the following results:

| Lipids | Relative Wet Combined Score |
|---|---|
| Isosteareth-2 | 4.5 |
| Isosteareth-10 | 4.0 |
| Petrolatum | 4.5 |
| Isostearyl lactate | 4.5 |
| Isopropyl isostearate | 4.5 |
| Isocetyl stearate | 4.5 |

EXAMPLE 2

The following shampoo formulation was prepared according to the procedure of Example 1:

| Ingredient | Tradename | Supplier | Wt. % |
|---|---|---|---|
| Part A | | | |
| Filtered Deionized Irradiated Water | | | QS |
| Hydroxyethyl Cellulose | Natrosol 250-HHR | Aqualon | 0.200 |
| Part B | | | |
| Ammonium Lauryl Sulfate | Standapol A, 28% | Henkel | 67.858 |
| Sodium Phosphate Monobasic | $NaH_2PO_4$ | J.T. Baker | 0.200 |
| Sodium Phosphate Dibasic | $Na_2HPO_4$ | J.T. Baker | 0.200 |
| Sodium Cumene Sulfonate | Naxonate SC, 98% | Reutgers-Nease | ±1.000 |
| Cocomidopropyl Betaine | Tego Betaine L-7 30% | Goldschmidt | 13.334 |
| Part C | | | |
| Propylene Glycol USP | Propylene Glycol USP | | 1.000 |
| Polyquaternium-10 | Polymer JR-30M | Amerchol | 0.300 |
| Quaternized Guar Gum | Cosmedia Guar C-261 | Henkel | 0.300 |
| Part D | | | |
| Paraffin Wax 128° F. | Boler 1070 | Boler Petroleum | 1.000 |
| $C_{20-40}$ Alcohol | Unilin 425 | Petrolite | 2.000 |
| Stearyl Alcohol | Adol 62 | Sherex | 2.000 |
| Tricetyl Ammonium Chloride | TC-90-F | Sherex | 2.000 |
| Distearyl Dimonium Chloride | Arosurf TA-100 | Sherex | 0.500 |
| Behenyl $C_{22}$-quat | Genamin KDM-F | BASF | 0.500 |
| Laureth-4 | Brij-30 | ICI | 0.500 |
| Hydrogenated Castor Oil | Cremophor RH-40 | BASF | 0.500 |
| Part E | | | |
| Perfume | | | 1.200 |
| Preservative | | | 0.750 |
| Blue Color (1% solution) | | | 0.021 |
| Green Color (1% solution) | | | 0.168 |
| TOTAL | | | 100.000 |

EXAMPLE 3

The following formulation was prepared according to the procedure of Example 1:

| Part | Ingredient | Supplier, Tradename | Wt. % |
|---|---|---|---|
| 1 | Deionized Water | | QS |
| | Sodium Deceth-3 Sulfate | Vista's Novel 10-44 E.S. Na, 30% | 6.000 |
| | Sodium Laureth-2 EO Sulfate | Henkel's Standepol ES-2 LV, 25% | 6.518 |
| | Sodium Laureth-3 Carboxylate | Sendoz's Sandopen L-24, 70% | 2.750 |
| | Cocoyl Sarcosine | Hampshire's Hamposyl C-Acid, 100% | 0.820 |
| | Na$_4$ EDTA | Rhone-Poulenc's Cheelox BF-78 | 0.090 |
| | Sodium Trideceth Sulfate | Rhone-Poulenc's Rhodopex EST-30, 30% | 11.900 |
| 2 | Cocoamphodiacetate | Niranol's C2N N.P., 38% | 9.200 |
| | Cocoamidopropyl Betaine No. 3 | Goldschmidt's Tego Betaine L-7, 30% | 13.750 |
| 3 | PEG-80 Sorbitan Laurate | ICI's Atias G-4280 | 9.000 |
| | Polyquaternium-10 | Amerchol's Polymer JR-30M | 0.275 |
| | Deionized Water | | 3.000 |
| | Sodium Cumene Sulfonate | Stepan's Stepanate SCS, 43% | 2.500 |
| | Polyquaternium-7 | | 3.450 |
| 4 | Isoateareth-2 | Sherex's Varonic 66-EZ (1.5 EO) | 1.850 |
| | Compound 909 | Petrolite's Polymer C-7138 | 4.100 |
| | Distearyl Dimonium Chloride | Sherex's Arosurf TA-100 | 0.900 |
| 5 | Colors | | QS |
| | Perfume | | 1.200 |
| | Preservative, 50% aqueous solution | | 1.000 |
| TOTAL | | | 100.000 |

EXAMPLE 4

The following formulations were prepared according to the above procedure and tested:

EXAMPLE 5

The following shampoo compositions were prepared according to the above-described procedure:

| Ingredient | Control | 1 | 2 | 3 | 4 | 5 | 6 | 7 | 8 | 9 | 10 |
|---|---|---|---|---|---|---|---|---|---|---|---|
| Part 1 | | | | | | | | | | | |
| Deionized Water | QS | QS | QS | QS | QS | QS | QS | QS | QS | QS | QS |
| ALS (28%) | 16.00 | 16.00 | 16.00 | 16.00 | 16.00 | 16.00 | 16.00 | 32.00 | 16.00 | 16.00 | — |
| SDES (30%) | 15.00 | 15.00 | 15.00 | 15.00 | 15.00 | 15.00 | 15.00 | 30.00 | 15.00 | 15.00 | — |
| Na$_4$ EDTA | 0.10 | 0.10 | 0.10 | 0.10 | 0.10 | 0.10 | 0.10 | 0.10 | 0.10 | 0.10 | 0.10 |
| Part 2 | | | | | | | | | | | |
| Betaine L-7 (30%) | 30.00 | 30.00 | 30.00 | 30.00 | 30.00 | 30.00 | 30.00 | — | 30.00 | 30.00 | 60.00 |
| Part 3 | | | | | | | | | | | |
| Deionized Water | 3.00 | — | 3.00 | 3.00 | 3.00 | 3.00 | 3.00 | 3.00. | 3.00 | — | 3.00 |
| Polyquaternium-10 | 0.30 | — | 0.30 | 0.30 | 0.30 | 0.30 | 0.30 | 0.30 | 1.00 | — | 0.30 |
| Part 4 | | | | | | | | | | | |
| SCS (43%) | 2.50 | 2.50 | 2.50 | 2.50 | 2.50 | 2.50 | 2.50 | 2.50 | 2.50 | 2.50 | 2.50 |
| Polyquaternium-7 (8%) | 3.75 | — | 3.75 | 3.75 | 3.75 | 3.75 | 3.75 | 3.75 | — | 7.50 | 3.75 |
| Part 5 | | | | | | | | | | | |
| Isosteareth-2 | 2.00 | 2.00 | — | 2.00 | — | 2.00 | — | 2.00 | 2.00 | 2.00 | 2.00 |
| Compound 909 | 4.00 | 4.00 | — | 4.00 | 4.00 | — | — | 4.00 | 4.00 | 4.00 | 4.00 |
| Distearyl DMAC | 0.90 | 0.90 | — | — | 0.90 | 0.90 | 0.90 | 0.90 | 0.90 | 0.90 | 0.90 |
| Part 6 | | | | | | | | | | | |
| Color, Perfume | QS | QS | QS | QS | QS | QS | QS | QS | QS | QS | QS |
| Preservative | 0.50 | 0.50 | 0.50 | 0.50 | 0.50 | 0.50 | 0.50 | 0.50 | 0.50 | 0.50 | 0.50 |
| Results of Lab Evaluations of Preceding Formulae on Virgin European Hair | | | | | | | | | | | |
| Wet Combing | 4.50 | 1.75 | 1.75 | 2.75 | 3.75 | 4.00 | 3.00 | 3.00 | 5.00+ | 4.50 | 3.00 |
| Dry Combing | 4.00 | 2.00 | 1.00 | 3.50 | 5.00 | 4.00 | 3.50 | 3.00 | 5.00 | 4.50 | 3.00 |
| Static Flyaway | No | No | Yes | Yes | No | No | No | No | No | No | No |
| Body | OK | OK | OK | OK | Less | OK | OK | OK | Less | Less | OK |
| Style Control | — | — | — | — | Good | — | — | — | Exc. | Good | — |

Those formulations that provide a high degree of style retention, such as Formulae Nos. 4, 8 and 9 of Example 4, were also found to be capable of repairing hair damage.

|  | Level | | | | |
|---|---|---|---|---|---|
| Ingredients | 1 | 2 | 3 | 4 | 5 |
| Part 1 | | | | | |
| Filtered Irradiated Deionized Water | QS | QS | QS | QS | QS |
| Hydroxyethyl Cellulose No. 2 | 0.7 | 0.7 | 0.6 | 0.3 | — |
| Ammonium Lauryl Sulfate, 28% | 12.0 | 12.0 | 12.0 | 12.0 | 12.0 |
| Sodium Deceth-3 Sulfate, 30% | 15.0 | 15.0 | 15.0 | 15.0 | 15.0 |
| Na$_4$ EDTA | 0.1 | 0.1 | 0.1 | 0.1 | 0.1 |
| Sodium Cumene Sulfonate, 43.3% | 4.5 | 4.5 | 4.5 | 5.0 | 6.5 |
| Cocoamidopropyl Betaine, 30% | 30.0 | 30.0 | 30.0 | 30.0 | 30.0 |
| Sodium Phosphate Dibasic | ±0.2 | ±0.2 | ±0.2 | ±0.2 | ±0.2 |
| Part 2 | | | | | |
| Filtered Irradiated Deionized Water | 3.0 | 3.0 | 5.0 | 8.0 | 10.0 |
| Polyquaternium-10 | 0.2 | 0.3 | 0.3 | 0.6 | 0.9 |
| Part 3 | | | | | |
| Isosteareth-2 | 0.8 | 0.8 | 0.8 | 0.8 | 0.8 |
| Compound 909 (Unilin) | 4.0 | 4.0 | 4.0 | 4.0 | 4.0 |
| Distearyl Dimonium Chloride | 1.0 | 1.0 | 1.0 | 1.0 | 1.0 |
| Part 4 | | | | | |
| Dimethicone/Polydimethyl Siloxane | 1.0 | 2.25 | 3.5 | 4.0 | 4.0 |
| Part 5 | | | | | |
| Blue Color (1% aqueous solution) | 0.021 | 0.021 | 0.021 | 0.021 | 0.021 |
| Green Color (1% aqueous solution) | 0.168 | 0.168 | 0.168 | 0.168 | 0.168 |
| Perfume | 1.2 | 1.2 | 1.2 | 1.2 | 1.2 |
| Preservative (50% aqueous solution) | 1.0 | 1.0 | 1.0 | 1.0 | 1.0 |
| Sodium Cumene Sulfonate, 93% | ±0.5 | ±0.5 | ±0.5 | ±0.5 | ±0.5 |
| TOTALS: | | | 100% EACH | | |

Each formulation was found to impart a high degree of hair conditioning and style control to hair shampooed therewith.

LOW SILICONE HAIR CONDITIONING SHAMPOO AND NON-SILICONE HAIR CONDITIONING/STYLE CONTROL SHAMPOO

We claim:

1. A hair conditioning shampoo composition comprising, by weight, an aqueous dispersion of:
   a) about 1% to about 16% of a water-insoluble lipid phase comprising a long chain aliphatic alcohol having an average of from about 24 to about 50 carbon atoms and from 0 to about 40 ethoxy units;
   b) at least about 0.7% of a water-insoluble, monocationic conditioner compound dissolved in said lipid phase, said monocationic compound being selected from the group consisting of an alkyl amine having a pKa of at least 7.5 selected from the group consisting of distearylamine, distearyl methylamine, behenylamine, behenylmethylamine, behenyldimethylamine, dicetylamine, dicetylmethylamine and tricetylamine;
   c) about 3% to about 25% of a water-soluble, anionic, hair cleansing organic surfactant;
   d) an amphoteric betaine or sulfobetaine surfactant containing a $C_8$-$C_{18}$ alkyl or $C_8$-$C_{18}$ alkanolamido $C_2$-$C_3$ alkylene group in its molecular structure, present in said dispersion at a level of at least 0.75 to 1.25 parts by weight per one part by weight of said anionic surfactant;
   e) from 0 to about 6% of a water-insoluble, non-volatile silicone hair conditioning agent; and
   f) 0.2% to 3% of at least one hair conditioning, water-soluble, film-forming polycationic polymer; the weight ratio of said monocationic conditioner compound to said lipid compound in said lipid phase being in the range of from about 5:1 to about 1:10 and the molar ratio of anionic surfactant to water-insoluble, monocationic compound being in the range of 2:1 to 50:1.

2. The shampoo according to claim 1 containing no silicone hair conditioning agent and possessing a high degree of hair conditioning and hair damage repair properties.

3. The shampoo according to claim 1 containing from about 0.2 to about 6% by weight, based on the weight of the shampoo, of said silicone and possessing a high degree of style control properties.

4. The shampoo of claim 1 wherein said anionic surfactant is an alkyl sulfate, alkyl ether sulfate, alkyl ether sulfonate, sulfate ester of an alkylphenoxy polyoxyethylene ethanol, alpha-olefin sulfonate, beta-alkoxy alkene sulfonate, alkyl arylsulfonate, sulfated monoglyceride, fatty acid amino polyoxyethylene sulfate or a combination thereof.

5. The shampoo of claim 1 wherein said anionic surfactant is ammonium lauryl sulfate.

6. The shampoo of claim 1 wherein said anionic surfactant is sodium decethsulfate.

7. The shampoo of claim 1 wherein said anionic surfactant is a mixture of ammonium lauryl sulfate and sodiumdecethsulfate.

8. The shampoo of claim 1 wherein said anionic surfactant is sodium laurethsulfate.

9. The shampoo of claim 1 wherein said lipid phase is said long chain aliphatic alcohol having an average of from about 24 to about 50 carbon atoms.

10. The shampoo of claim 1 wherein said hair conditioning monocatronic compound comprises from about 0.7% to about 3% by weight of said shampoo.

11. The shampoo of claim 4 wherein said amphoteric surfactant is cocoamidopropyl betaine.

12. The shampoo of claim 1 additionally containing a hydrotrope selected from the group consisting of sodium cumene sulfonate, sodium xylene sulfonate, sodium benzene sulfonate and sodium hexyl sulfate.

13. The shampoo of claim 1 wherein said water soluble cationic polymer comprises a salt of hydroxyethyl cellulose reacted with a trimethyl ammonium substituted epoxide.

14. The shampoo of claim 1 wherein said water soluble cationic polymer comprises a copolymer of acrylamide and dimethyldiallylammonium chloride.

15. The shampoo of claim 2 wherein said anionic surfactant is selected from the group consisting of a $C_8$–$C_{18}$ alkyl sulfate, a $C_8$–$C_{18}$ alkyl ether ethenoxy sulfate containing 1–12 ethenoxy groups and mixtures thereof and is present in an amount of 7% to 14% by weight; said amphoteric surfactant is said betaine; and said water-insoluble lipid phase is present in an amount of 4% to 10% by weight.

16. The shampoo of claim 15 wherein said polycationic polymer is selected from the group consisting of a salt of hydroxyethyl cellulose reacted with a trimethyl ammonium substituted epoxide, a copolymer of acrylamide and dimethyldiallylammonium chloride and mixtures thereof.

17. The shampoo of claim 16 wherein said lipid phase comprises a mixture of said long chain alcohol and isostearyl alcohol ethoxylate.

18. The shampoo of claim 1 wherein said lipid phase includes an ethoxylated isostearyl alcohol.

* * * * *